United States Patent [19]

Schäfer

[11] 4,295,592
[45] Oct. 20, 1981

[54] APPARATUS FOR JOINING AND CLADDING PIPE SECTIONS

[75] Inventor: August W. Schäfer, Wilnsdorf-Wilden, Fed. Rep. of Germany

[73] Assignee: Wilhelm Schäfer Maschinenbau, Wilnsdorf-Wilden, Fed. Rep. of Germany

[21] Appl. No.: 82,624

[22] Filed: Oct. 9, 1979

[30] Foreign Application Priority Data

Nov. 4, 1978 [DE] Fed. Rep. of Germany ....... 2847966

[51] Int. Cl.³ .................. B23K 37/02; B23K 37/04
[52] U.S. Cl. .................................. 228/17; 228/17.7; 228/45; 228/48; 228/173 D
[58] Field of Search .............. 228/45, 48, 173 D, 15.1, 228/17, 17.7, 145; 219/62

[56] References Cited

U.S. PATENT DOCUMENTS

| 2,600,630 | 6/1952 | Fergusson ...................... 228/145 X |
| 2,749,421 | 8/1956 | Mikulak et al. .................... 228/45 X |
| 3,549,077 | 12/1970 | Huck .................................. 228/17.7 |
| 3,715,557 | 2/1973 | Netterstedt et al. .................. 219/62 |
| 4,121,746 | 10/1978 | Frohlich et al. .................. 228/48 X |

FOREIGN PATENT DOCUMENTS 724657 9/1942 Fed. Rep. of Germany.

Primary Examiner—Howard N. Goldberg
Assistant Examiner—K. J. Ramsey
Attorney, Agent, or Firm—Karl F. Ross

[57] ABSTRACT

An apparatus for joining and cladding pipe sections has a cradle which holds two cylindrical pipe sections with their ends abutting axially and their axes coaxially horizontally aligned. A carriage is displaceable axially adjacent the cradle and carries a primary welding tool which can weld the ends of the pipe sections together as they are rotated in the cradle. Metal strip can be pulled of a supply of strip on the carriage, bent into a U-section, arced, and helically applied to the pipe sections as they rotate. Meanwhile a second welding tool on the carriage welds the arced U-section strip to the pipe sections as they rotate to form a helical passage therealong.

6 Claims, 2 Drawing Figures

APPARATUS FOR JOINING AND CLADDING PIPE SECTIONS

FIELD OF THE INVENTION

The present invention relates to an apparatus for joining and cladding pipe sections. More particularly this invention concerns such an apparatus used for pipe sections of large diameter, more than 2 m, whose cladding forms with the joined pipe sections a helical passage.

BACKGROUND OF THE INVENTION

In order to form large containers or conduits whose walls can be heated or cooled, it is known to join large-diameter pipe sections and then to clad the joined sections with a strip that forms with them a helical passage. The strip and pipe sections are formed of a weldable metal, normally steel.

As a rule the pipe sections are secured together by an apparatus which positions two pipe sections adjacent each other with their axes aligned and their ends abutting. The two pipe sections are then normally jointly rotated adjacent a welding tool which seams the two ends together.

Subsequently the joined sections are normally moved to a location where a U-section metal strip is manually wound helically around the joined sections and joined thereto along the strip edges. As a rule the strip is merely temporarily secured to the joined pipe sections, then the entire assembly is heat treated to eliminate stresses, and subsequently the two edges of the strip are welded in continuous seams to the outer surface of the joined pipe sections.

Obviously the cost of making such an item is extremely high. In addition the product is often unsatisfactory, in that the welds joining the U-section strip to the joined pipe sections are relatively failure prone, frequently developing leaks and requiring subsequent expensive repair.

OBJECTS OF THE INVENTION

It is therefore an object of the present invention to provide an improved apparatus for joining and cladding pipe sections.

Another object is to provide such a system which allows the pipe sections to be joined and helically clad with a U-section strip at relatively low cost.

SUMMARY OF THE INVENTION

These objects are attained in accordance with the instant invention in an apparatus of the above-described general type wherein two pipe sections are held with their axes coaxial and horizontal and with their ends in abutment in a cradle, and are rotated in this cradle adjacent a fixed welding tool mounted on a carriage displaceable axially along the cradle. According to this invention a supply of metal strip is carried on the carriage and means is provided on the carriage for withdrawing the strip from the supply, arcing the strip to a radius of curvature substantially equal to that of the pipe sections, and helically applying the arced strip to the pipe sections as they are rotated. A secondary welding tool on the carriage welds the arced strip helically to the pipe as the pipe is rotated and control means synchronously axially displaces the carriage and rotates the pipe sections during welding of the arced strip to the sections.

Thus a relatively straightforward apparatus is capable of performing the major operations for joining together a pair of pipe sections and helically winding a cladding strip therearound. As the two operations can follow each other in close succession the possibility of the pipe sections oxydizing and weakening the welds joining the helical strips thereto is largely ruled out. In addition the arcing of the strip prior to applying it to the tube ensures that it will lie closely thereagainst, so that the normally required heat-treating operation becomes unnecessary.

According to further features of this invention the carriage has an upright post with a horizontal outrigger whose end carries the two welding tools. The outrigger is vertically displaceable on the post and the tools are either horizontally displaceable on the traverse on the outrigger or the outrigger is also horizontally displaceable on the post. Normally the arrangement is set up so that the tools are at the uppermost portion of the pipe sections being worked on, the welding torches therefore being directed vertically downwardly.

It is also possible according to this invention to form the helical strip completely right on the carriage. Thus a coil of flat steel strip is mounted on the carriage. The strip is pulled off the coil and leveled, then is bent into a U-section, and subsequently is arced to a radius of curvature equal to that of the pipe section. All of these operations take place directly on the carriage as same moves along the pipe sections which are being rotated about their horizontal axes. Meanwhile the welding tool at the top of the carriage is seaming the thus formed U-section arced strip to the pipe sections. The bending and arcing device can according to another feature of this invention be mounted on a support pivotal about a horizontal axis parallel to the axes of the pipe sections. A hydraulic or pneumatic cylinder connected between the support and the carriage pivots the support on the carriage so that the arced U-section strip will meet the joined pipe sections at an angle exactly tangent to them at the welding tool. In this manner the apparatus can be adjusted to accommodate pipes of different diameters.

SPECIFIC DESCRIPTION

Figure 1:
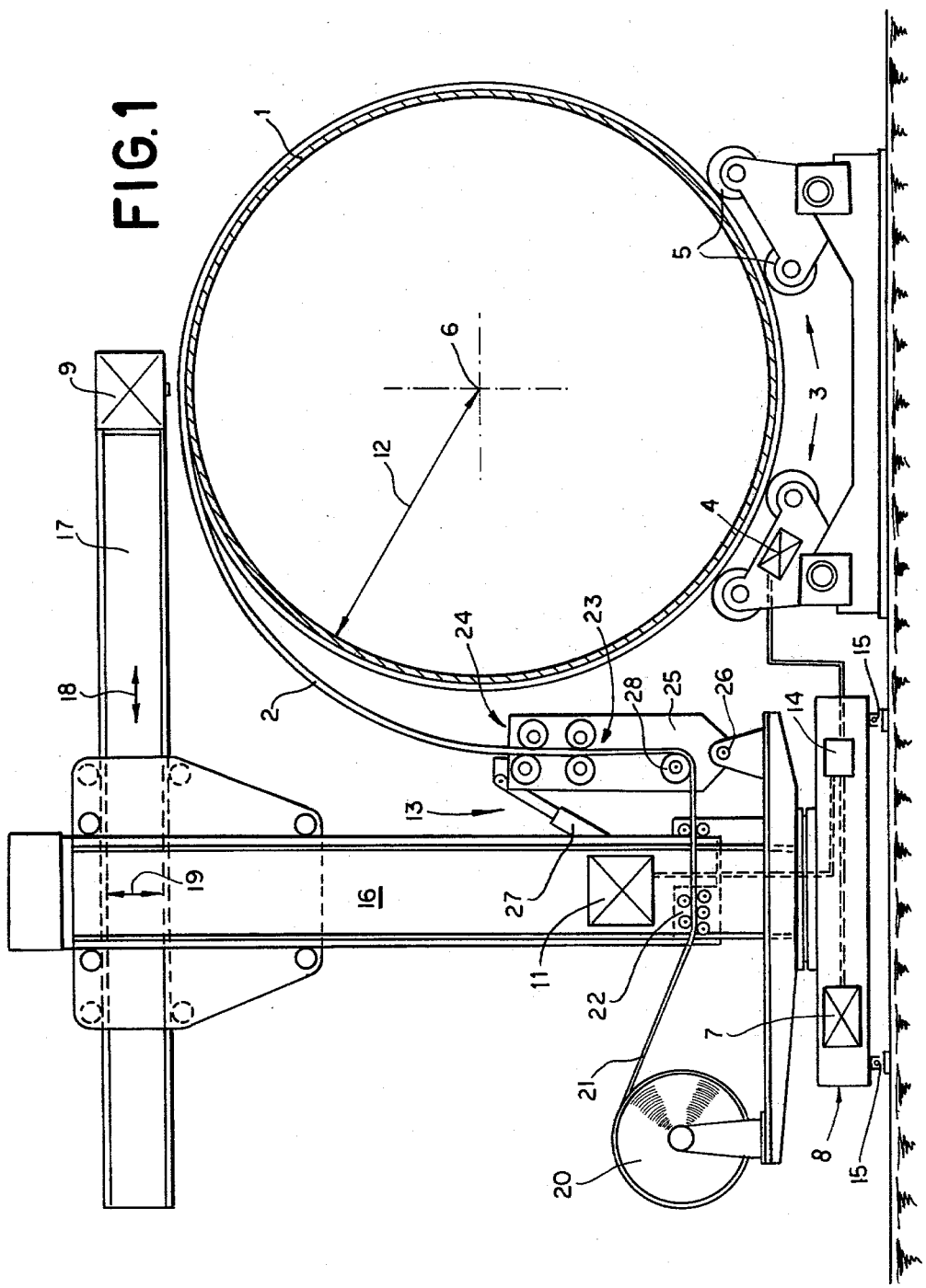
FIG. 1 is an end view of the apparatus according to this invention.
Figure 2:
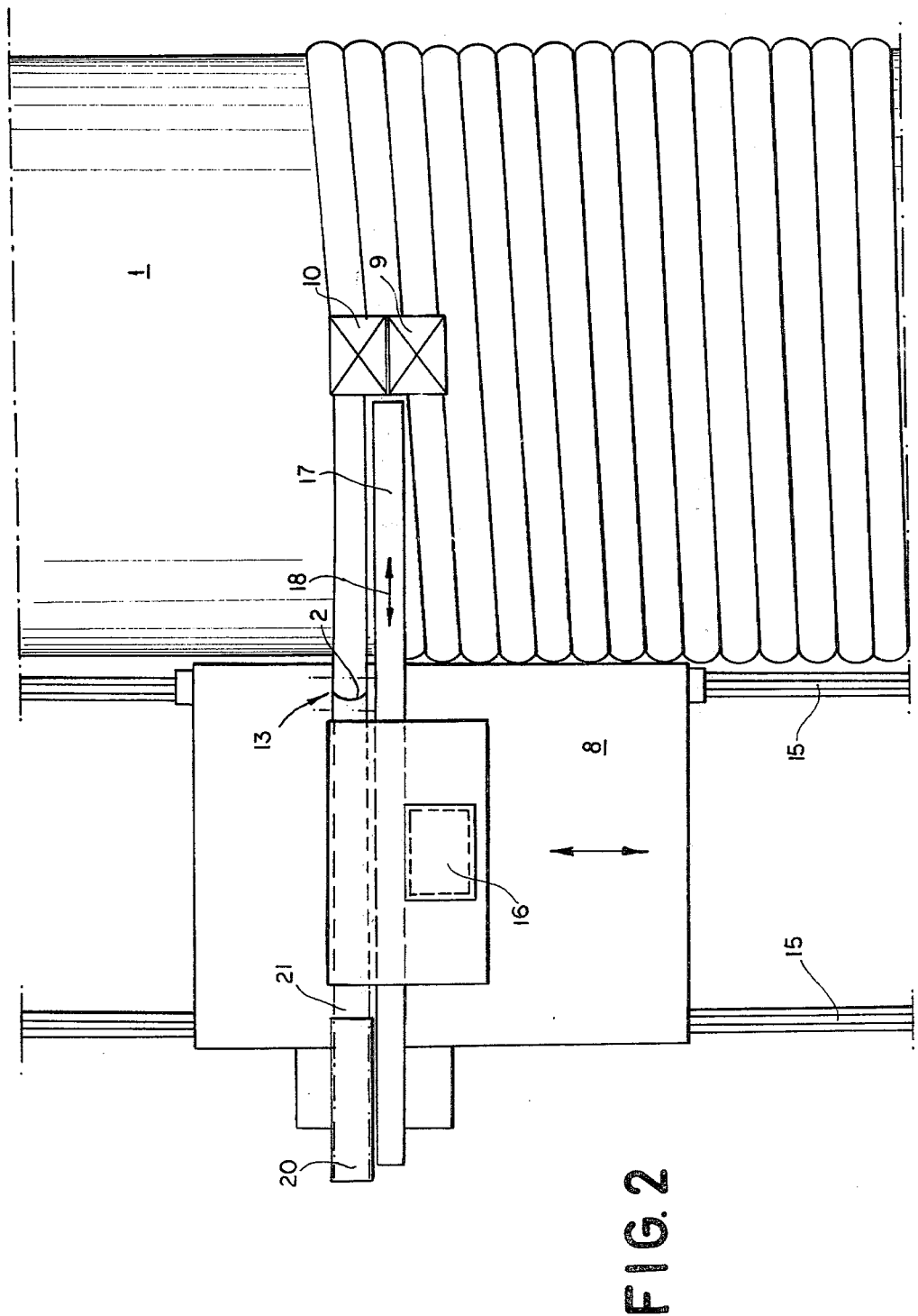
FIG. 2 is a top view of the apparatus of FIG. 1.

As shown in the drawing the apparatus according to this invention basically serves to join together a plurality of identical cylindrical pipe sections 1 and to wind helically about the joined sections a U-section steel band 2. To this end the device has a cradle 3 whose rollers 5 are coupled to a drive 4 so that a plurality of sections 1 can be rotated about the horizontal longitudinal axes 6 of the sections 1.

A carriage 8 is displaceable by means of a hydraulic drive 7 along tracks 15 extending parallel to the axis 6. This carriage 8 carries a welder 9 that serves to butt-weld two tube sections 1 together, and another welding tool 10 that serves to secure the longitudinal edges of the U-section arc strip 2 to the joined sections 1.

According to the instant invention the carriage 8 has an upright post 16 carrying a horizontal outrigger 17. The outrigger 17, formed by an I-beam, is horizontally displaceable relative to the post 16 as indicated by arrow 18 and is similarly vertically displaceable relative to the post 16 as indicated by the arrow 19. Thus the welding tools 9 and 10 can be positioned above the uppermost portion of a tube 1 of any given diameter, and are normally positioned directly above the axis 6 thereof.

The carriage 8 carries a reel 20 of a flat steel band 21 that is passed through a roller-type leveler 22 and then around a deflection roller 28 to a pair of bending rollers 23 and thence through a pair of arcing rollers 24. A drive 11 operates the devices 22-24 and is coupled to a central controller 14 that ensures that the band 21 is pulled off the coil 20 at a rate exactly equal to the peripheral speed of the tube sections 1. Thus the devices 22-24 constitute a feed 13 which takes a flat band 21 and converts it into a U-section arced band 2 having a radius 12 of curvature equal exactly to the radius of curvature of the pipe sections 1.

The various rollers 23, 24 and 28 are all mounted on a support plate 25 pivotal about a horizontal axis 26 parallel to the axis 6 and positionable by means of a hydraulic ram or cylinder 27 connected to the post 16. In this manner the U-section arced strip 2 will meet the tube sections 1 tangentially at the extreme uppermost portions thereof. In use a plurality of pipe sections 1 are laid on the cradle 3 and the drive 4 operates the rollers 5 to rotate them jointly while the welding tool 9 butt-welds their ends together. Once they are joined together the entire carriage 8 is moved to one end of the joined pipe sections and the controller 14 then operates the feed 13 as well as the drives 4 and 7 and the welding tool 10 to U-section and arc the band 21 and apply it helically to the joined tube sections 1. The rate of advance is equal to the pitch of the helix of the strip wound on the tube sections 1 so that the welder 10 need merely form a continuous helical weld which joins the upstream edge of the furthest downstream turn along with the upstream edge of the next closest turn to the tube sections 1 simultaneously.

The device according to the instant invention could, of course, be set up to apply the U-section arced strip 2 to a location on the pipe sections 1 horizontally in line with the axis 6 thereof. Similarly the axis 6 does not have to be perfectly horizontal.

In any case the device according to the instant invention is capable of rapidly and easily producing an elongated cylindrical pipe or container formed of a plurality of pipe sections welded together at their ends and wrapped with a strip that forms a helical passage on the pipe sections. Such an arrangement can readily be used as a cooled or heated conduit or storage vessel.

I claim:

1. An apparatus for joining pipe sections and for forming around the joined pipe sections a helical passage, said apparatus comprising:
    means including a cradle for holding two cylindrical pipe sections with their ends abutting axially and their axes coaxial;
    means including a roller in said cradle for jointly rotating said sections about said axes with said ends abutting;
    a track extending parallel to said axes;
    a carriage displaceable axially on said track adjacent said cradle and including an upright post and a horizontal outrigger carried on said post;
    means including a primary welding tool on said carriage for welding together the ends of said pipe sections as same rotate;
    a supply of flat metal strip on said carriage;
    means on said carriage for withdrawing said strip from said supply, bending said strip into a U-section, arcing said strip to a radius of curvature substantially equal to that of said sections, and helically applying the arced strip to said pipe sections as same rotate with the concave side of said strip turned toward said sections, whereby said strip forms with said sections a helical passage;
    means including a secondary welding tool on said carriage for welding the arced strip helically to said pipe sections as same rotate;
    means for vertically displacing said outrigger on said post for displacing said tools radially of said axes and for retaining said tools in any of a multiplicity of radially offset positions on said carriage, said tools being downwardly directed and effective, whereby welding is effected at the highest parts of said sections; and
    control means connected to all of said means for synchronously axially displacing said carriage on said track and rotating said pipe sections during welding of the arced and U-section strip to said sections.

2. The apparatus defined in claim 1, further comprising means on said carriage for leveling said strip prior to U-bending of same.

3. The apparatus defined in claim 1 wherein said carriage has a support swingable about a support axis substantially parallel to the axes of said sections, said means for bending and arcing being carried on said support.

4. The apparatus defined in claim 3 wherein said means for bending and arcing include driven rollers.

5. The apparatus defined in claim 1 wherein said welding tools are fixed together for joint displacement.

6. The apparatus defined in claim 1 wherein said cradle is horizontal so said axes are horizontal.

* * * * *